(12) United States Patent
Stender et al.

(10) Patent No.: US 11,559,644 B2
(45) Date of Patent: Jan. 24, 2023

(54) PROCESS AND ADJUSTING DEVICE FOR ADJUSTING A VENTILATION PARAMETER AS WELL AS MEDICAL SYSTEM

(71) Applicant: Drägerwerk AG & Co. KGaA, Lübeck (DE)

(72) Inventors: Birgit Stender, Lübeck (DE); Christian Bozsak, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 834 days.

(21) Appl. No.: 16/506,204

(22) Filed: Jul. 9, 2019

(65) Prior Publication Data

US 2020/0016352 A1 Jan. 16, 2020

(30) Foreign Application Priority Data

Jul. 10, 2018 (DE) ..................... 10 2018 005 433.1

(51) Int. Cl.
*A61M 16/00* (2006.01)
*A61B 5/0536* (2021.01)
(Continued)

(52) U.S. Cl.
CPC ......... *A61M 16/024* (2017.08); *A61B 5/0536* (2013.01); *A61B 5/0809* (2013.01);
(Continued)

(58) Field of Classification Search
CPC ........ A61M 16/024; A61M 2016/0018; A61M 2016/0027; A61M 2016/0036; A61M 2205/52; A61M 2016/0021; A61M 2016/1025; A61M 2205/3344; A61M 2205/3592; A61M 2205/505; A61M 2205/581; A61M 2205/583; A61M 2230/202; A61M 2230/205; A61M 2230/432; A61M 2230/65; A61B 5/0536;
(Continued)

(56) References Cited

U.S. PATENT DOCUMENTS 9,987,446 B2 6/2018 Novotni et al.
11,278,246 B1 * 3/2022 McNair ................ A61B 5/0816
(Continued)

FOREIGN PATENT DOCUMENTS

DE 102016107603 A1 10/2017

*Primary Examiner* — Kendra D Carter
*Assistant Examiner* — Arielle Wolff
(74) *Attorney, Agent, or Firm* — McGlew and Tuttle, P.C.

(57) ABSTRACT

A process adjusts a ventilation parameter (40) for a ventilation process (90) of a patient (110), which is carried out by a ventilator (20). Electrical impedance tomographic (EIT) data (70) of the lungs (111) of the patient (110), concerning the ventilation process (90), are collected by an EIT device (30). An adjusting device (1), adjusting a ventilation parameter (40) for the ventilation process (90), has an analysis unit (2) with a memory (3), a data input unit (5) data-communicatingly connected to the analysis unit (2) for receiving data and a data output unit (7) data-communicatingly connected to the analysis unit (2) for outputting data. A medical system (100), includes a ventilator (20), an EIT device (30) as well as the adjusting device (1) for adjusting a ventilation parameter (40) for the ventilation process (90) of a patient (100).

23 Claims, 10 Drawing Sheets

(51) Int. Cl.
    *G16H 40/60*         (2018.01)
    *A61B 5/08*          (2006.01)
    *G16H 10/60*         (2018.01)

(52) U.S. Cl.
    CPC ..... *G16H 40/60* (2018.01); *A61M 2016/0018* (2013.01); *A61M 2016/0027* (2013.01); *A61M 2016/0036* (2013.01); *A61M 2205/52* (2013.01); *G16H 10/60* (2018.01)

(58) Field of Classification Search
    CPC ... A61B 5/0809; A61B 5/03; A61B 2562/043; A61B 5/0035; A61B 5/0816; A61B 5/14542; A61B 5/6823; G16H 40/60; G16H 10/60; G16H 20/40
    See application file for complete search history.

(56) References Cited

U.S. PATENT DOCUMENTS

| | | | |
|---|---|---|---|
| 2014/0207005 A1* | 7/2014 | Bukkapatnam | A61B 5/318 600/509 |
| 2015/0379706 A1* | 12/2015 | Leonhardt | A61B 6/032 382/131 |
| 2019/0125277 A1* | 5/2019 | Radke | A61B 5/0036 |
| 2021/0069436 A1* | 3/2021 | Friberg | G06F 3/03547 |

\* cited by examiner

PROCESS AND ADJUSTING DEVICE FOR ADJUSTING A VENTILATION PARAMETER AS WELL AS MEDICAL SYSTEM

CROSS REFERENCE TO RELATED APPLICATIONS

This application claims the benefit of priority under 35 U.S.C. § 119 of German Application 10 2018 005 433.1, filed Jul. 10, 2018, the entire contents of which are incorporated herein by reference.

TECHNICAL FIELD

The present invention pertains to a process for adjusting a ventilation parameter for a ventilation process of a patient, wherein the ventilation process is carried out by a ventilator, and wherein electrical impedance tomography data (EIT data) of the lungs of the patient are, furthermore, collected by an EIT device at least from time to time. The present invention further pertains to an adjusting device for adjusting a ventilation parameter for a ventilation process of a patient, having an analysis unit with a memory, a data input unit connected to the analysis unit in a data-communicating manner for receiving data and a data output unit connected to the analysis unit in a data-communicating manner for outputting data. According to another aspect, the present invention pertains to a medical system, having a ventilator, an EIT device as well as an adjusting device for adjusting a ventilation parameter for a ventilation process of a patient.

TECHNICAL BACKGROUND

It is known, in principle, in the medical care of patients that a patient is ventilated, if necessary, mechanically by a ventilator. This ventilation process is determined mostly by a plurality of ventilation parameters, which can be set especially by the staff operating the ventilator, for example, physicians and/or nursing staff. To make it possible to provide an as optimal a ventilation as possible for the patient, these ventilation parameters are often set according to the knowledge of the professional staff and/or changed iteratively while observing the patient in order to determine an at least essentially optimal value of the ventilation parameters for the ventilation process of the patient in question.

Furthermore, devices for electrical impedance tomography are known from the state of the art. These devices are configured and provided by means of an array of electrodes to generate an image, a plurality of images or a continuous sequence of images by means of an image reconstruction algorithm from signals obtained by means of electrical impedance measurements and data streams obtained therefrom. These images or image sequences may show especially changes in the conductivity of different tissues of the body, for example, of the blood in the lungs and heart, as well as of breathing air in the lungs in an axial projection plane. These images are useful for the assessment of states of the lungs, especially with regard to the distribution of blood perfusion (regional perfusion of the lungs, hereinafter called perfusion distribution for short) and the distribution of the tidal volume and hence of the respiratory minute volume (regional alveolar ventilation, hereinafter called ventilation distribution for short) of the lungs or of the lung tissue, as well as of states of the heart, especially by an analysis of the changes in the blood volumes in certain ventricles of the heart.

SUMMARY

Based on this state of the art, a basic object of the present invention is to improve processes for adjusting a ventilation parameter for a ventilation process of a patient, adjusting devices for adjusting a ventilation parameter of a ventilation process of a patient as well as medical systems. The object of the present invention is, in particular, to provide a process, an adjusting device as well as a medical system, which make possible or at least improve, especially automate, the setting of a ventilation parameter for a ventilation process in an especially simple and cost-effective manner, wherein an EIT device shall preferably be used as a data basis for the optimization of the ventilation parameter of the ventilation process.

The above object is accomplished by a process for adjusting a ventilation parameter for a ventilation process of a patient having features according to the invention, by an adjusting device for adjusting a ventilation parameter for a ventilation process of a patient having features according to the invention as well as by a medical system having features according to the invention. Further features and details of the present invention appear from the description and from the drawings. Features and details that are described in connection with the process according to the present invention are, of course, also valid in connection with the adjusting device according to the present invention as well as with the medical system according to the present invention as well as vise versa, so that reference is and can always mutually be made to the individual aspects of the present invention concerning the disclosure.

According to a first aspect of the present invention, the object is accomplished by a process for adjusting a ventilation parameter for a ventilation process of a patient, wherein the ventilation process is carried out by a ventilator, and wherein electrical impedance tomography data (EIT data) of the lungs of the patient, which data concern the ventilation process, are collected by an EIT device at least from time to time. A process according to the present invention is characterized by the following steps:

a) Setting of the ventilation parameter of the ventilation process, which parameter is to be adjusted, and/or of a ventilation parameter to be adjusted, as well as of a ventilation target variable for indicating the ventilation process and/or the ventilation parameter, b) setting of a variation procedure of a variation of the ventilation parameter set in step a), comprising at least two variation sections with a respective different variation value of the ventilation parameter each, c) carrying out of the variation of the ventilation parameter set in step a) on the basis of the variation procedure set in step b), wherein EIT data of the patient are collected by the EIT device for each of the at least two variation sections, d) determining of a ventilation distribution in the lungs and of a perfusion distribution in the lungs from the EIT data collected in step c) for each of the at least two variation sections carried out in step c), e) comparing of the ventilation distributions and perfusion distributions determined for each of the at least two variation sections carried out in step d) for determining a quality parameter of the ventilation process in each of the at least two variation sections, wherein the quality parameter corresponds or at least essentially corresponds to a similarity of the respective ventilation distribution and perfusion distribution, f) determining of the variation section with the best quality parameter by comparing the at least two variation sections carried out in step e) for each of the at least two variation sections carried out in step c), and g) outputting of the variation value of the variation section determined in step f) as a parameter value for the ventilation parameter to be set, which was set in step a).

The ventilation of a patient by a ventilator requires an individual setting and especially a continual checking or monitoring. The ventilation process is determined especially by at least one ventilation parameter, whose parameter value can and must be coordinated with the patient in question. According to a process according to the present invention, this setting can be carried at least partially in an automated manner and is carried out, moreover, especially with the use of an EIT device. EIT data of a lung region of the patient in question, which make it possible especially to infer a ventilation distribution in the lungs and a perfusion distribution in the lungs, more precisely in the lung tissue of the patient in question, can be collected by such an EIT device. The individual steps of the process according to the present invention and details and special advantages thereof will be described below in detail.

In a first step a) of a process according to the present invention, the ventilation parameter to be adjusted is set. The ventilation parameter that shall be adjusted by the process according to the present invention and the ventilation parameter for which a parameter value fitting as much as possible are thus set already in this first step a) of a process according to the present invention. In particular, the ventilation parameter itself or, in addition to the ventilation parameter, also a ventilation target variable, which can be used to indicate the ventilation process and/or the ventilation parameter, may be set in the course of this step. In other words, it is possible to set directly the ventilation parameter as the only set variable at the beginning of the process according to the present invention, or to also indicate, as an alternative and/or in addition to the ventilation parameter, a ventilation target variable, which is configured to indicate, i.e., to preferably unambiguously describe the ventilation process and/or the ventilation parameter. The setting of such a ventilation target variable is especially advantageous if the ventilation parameter itself cannot be checked or monitored or can only be checked or monitored with difficulty and can nevertheless be described at least indirectly by the ventilation target variable.

In a second step b) of a process according to the present invention, a variation procedure of a variation, which shall be carried out for the ventilation parameter set in step a), is now set. The set variation procedure of the variation comprises, in particular, at least two and preferably more than two variation sections, in which a respective different variation value of the ventilation parameter shall be used. In other words, a ventilation process of the patient is carried out during the entire variation, and the ventilation is carried out with different values of the ventilation parameter for each of the variation sections, the particular value of the ventilation parameter in the individual variation sections corresponding to the variation values set in step b).

This variation set in step b) with its variation procedure is carried out in a next step c) of a process according to the present invention. The ventilation process of the patient is thus carried out in this step c) with the use of the variation values of the ventilation parameter for the individual variation sections. At the same time, at least one EIT data set of EIT data of the patient is collected by the EIT device for each of the variation sections. In other words, EIT data of the patient, especially of the thorax of the patient, are thus available for each of the variation values of the ventilation parameter, which variation values are used in the variation, after carrying out step c).

This is used in the next step d) of a process according to the present invention in order to determine a ventilation distribution in the lungs and a perfusion distribution in the lungs or in the lung tissue of the patient from the EIT data for each variation section. Information showing, especially correlated with the respective variation values of the ventilation parameter, how the air distribution and the blood distribution change in the lungs of the patient when the variation of the ventilation process is carried out is thus available after step d) of a process according to the present invention.

In the next step e) of a process according to the present invention, these ventilation distributions and perfusion distributions determined in step d) of a process according to the present invention are now compared with one another for each of the individual variation sections performed. This comparison is based especially on the consideration that good ventilation of the patient is especially present or can be assumed to be present at a high level of probability if good gas exchange can take place in the patient's lungs between the air in the lungs and the blood in the lungs. Such a gas exchange is, however, especially effective whenever locations in the lungs at which the quantity of the new arriving gas volume per unit of time is high also have good blood perfusion at the same time, in other words, if a high volume flow of blood, preferably an approximately equally high volume flow of blood, is also present at these locations. This criterion can be checked especially by determining degree to which the two distributions, namely, the ventilation distribution and the perfusion distribution, agree. The comparison of the ventilation distributions and perfusion distributions determined in respect to their agreement thus yields a quality parameter, which corresponds or at least essentially corresponds, in turn, to a similarity of the respective ventilation distributions and perfusion distributions. In other words, an especially high quality parameter can correspond, for example, to an especially close similarity and a lower quality parameter to a less marked similarity of the compared ventilation and perfusion distributions in the lungs or in the lung tissue.

To make it now possible to set an especially good ventilation parameter by a process according to the present invention, the variation section with the best quality parameter is determined in the next step f) of a process according to the present invention. This is carried out especially by a comparison of the quality parameters determined, with a quality parameter being available for each of the variation sections carried out. The quality parameters determined in step e) correspond at least essentially to a similarity of the respective distributions compared, and the quality parameter becomes better with increasing similarity of the respective ventilation distribution and perfusion distribution compared. The quality parameter whose value reflects the closest similarity of all compared pairs of distributions is thus set as the best quality parameter in step f) of a process according to the present invention. In other words, information showing the particular variation sections in which the best quality parameter was reached or the variation sections in which the ventilation distribution and the perfusion distribution in the patient's lungs had the closest similarity is thus available after carrying out step f) of a process according to the present invention.

This variation value of the variation section of the ventilation parameter, which variation section was determined in step f), is outputted in the last step g) of a process according to the present invention as the parameter value for the ventilation parameter set at the beginning of the process according to the present invention. This parameter value can now be used for the ventilation of the patient to be performed in the future, as a result of which the value that is most effective for the ventilation among the variation values being considered and hence the best ventilation can be provided.

In summary, a setting of a ventilation parameter of a ventilation process of a patient can thus be improved by a process according to the present invention. In particular, the entire process may also be carried out in an automated or at least partially automated manner by corresponding devices by setting, for example, the individual variation sections of the variation procedure after a manual input of the ventilation parameter to be set as well as by carrying out the variation of the ventilation process by the corresponding devices. Provisions may also be made for carrying out a process in a fully automated manner without the obligatory presence of a professional staff, for example, at regular time intervals for the continuous re-optimization of the settings of the ventilator while the patient's lungs or pulmonary function undergo changes over time. In particular, an effect of the change in the used value of the ventilation parameter to be adjusted can be determined and monitored in real time. By using the EIT device, this can also be carried out, in particular, directly at the hospital bed, without the patient having to be brought to the corresponding imaging devices, for example, a CT device or a PET device, for example, for medical imaging. Imaging that is suitable for a continuous monitoring is especially advantageous in the case of patients who require intensive care. Moreover, provisions may also be made for the entire process or at least parts of it to be stored in a corresponding machine-readable memory.

Further, provisions may be made in a process according to the present invention for at least one of the following ventilation parameters to be set in step a):
positive end-expiratory pressure (PEEP),
inspiratory pressure,
tidal volume,
ventilation rate,
inhalation/exhalation ratio (I:E),
$FiO_2$ and
minute volume.

This list is specifically incomplete, so that additional ventilation parameters may also be set in step a) of a process according to the present invention. A positive end-expiratory pressure (PEEP) describes especially the gas pressure that becomes established in the patient's lungs at the end of an exhalation process. The setting of a suitable PEEP prevents the collapse of lung regions, which would then cease to be available for a further alveolar ventilation. The inspiratory pressure describes the pressure of the breathing air provided during the ventilation process. The tidal volume designates the fresh gas volume provided during one breath. A ventilation rate describes, in turn, a number of breaths that are performed by the ventilator for the patient per unit of time. The product of the ventilation rate and the tidal volume determines the alveolar ventilation in case of purely mandatory (purely mechanically preset) forms of ventilation. If the ventilation rate is selected to be too low at a functional tidal volume, the alveolar ventilation is not suitable in the first step for removing the carbon dioxide produced by the body in the blood. The oxygen supply of the patient may also drop in the second step, which is also dependent on the relative percentage of oxygen in the inhaled gas. If the ventilation rate is selected to be too high, the effectiveness of the ventilation decreases, because the relative percentage of the ventilation is too high in regions of the upper airways that do not participate in the gas exchange at all compared to an optimal ventilation rate. The inhalation time/exhalation time ratio describes, in turn, the ratio of the duration of the phase of inhalation to the duration of the phase of exhalation during an individual breath. The $FiO_2$ designates the relative percentage of oxygen in the inspiratory gas volume flow. The minute volume describes, in turn, the gas volume that is provided for the patient by the ventilator per minute during a ventilation process. A reduced value of these parameters may be set depending on the selected form of ventilation.

A process according to the present invention may also be configured such that at least one of the following indicating ventilation target variables is set in step a):
alveolar minute volume,
mean airway pressure,
mean intrathoracic pressure,
(arterial) oxygen saturation and oxygen partial pressure and
(arterial or end-tidal) concentration or partial pressure of carbon dioxide.

This list is incomplete as well, so that additional indicating ventilation target variables may also be set in step a) of a process according to the present invention. Ventilation target variables represent especially target variables that can be monitored during a ventilation process but cannot be set directly as ventilation parameters. The alveolar minute volume designates the minute volume actually applied by the ventilator minus the percentage of ventilation in the upper airways, i.e., where a ventilation does not contribute to the gas exchange. The mean airway pressure is thus obtained as an interaction of the ventilation pressure due to the ventilator and the resulting response of the patient, which response acts thereon. The mean intrathoracic pressure is obtained as a pressure difference between an external pressure and the pressure in the patient's pleural space, the space between the thorax and the lungs. This intrathoracic pressure can be determined, for example, by a direct measurement by means of pleurocentesis, but this pleurocentesis, being an invasive procedure, involves risks. An equivalent measurement of the intrathoracic pressure may be carried out by means of a corresponding catheter in the esophagus of the patient. An (arterial) oxygen saturation indicates the percentage of hemoglobin in the (arterial) blood of the patient that is saturated with oxygen. Such an oxygen saturation may be determined, for example, by a pulse oximeter, especially by a finger clip pulse oximeter. The pressure that the oxygen dissolved in the blood or the carbon dioxide dissolved in the blood has compared to the pressure of all the gases dissolved in the blood is called the partial pressure, especially of oxygen and/or carbon dioxide. The oxygen and carbon dioxide partial pressures are measured mostly via a blood gas analysis or else also by a corresponding skin probe, for example, in the bend of the elbow. Target areas for the (arterial) oxygen saturation and the (arterial) oxygen partial pressure are often patient-dependent, for example, based on the patient's age and the underlying health status of the patient. For example, young healthy patients who are ventilated with ambient air should thus have an oxygen saturation of more than 95% and preferably close to 100%. A preferred target range of 70-90 mmHg is obtained for the arterial oxygen partial pressure for these patients. A target range of 35-45 mmHg is correspondingly obtained for a partial pressure of the carbon dioxide.

A process according to the present invention may be further perfected, in particular, such that a combination of at least two ventilation parameters to be set and/or a combination of at least two indicated ventilation target variables and/or a combination of at least one ventilation parameter to be set and at least one indicating ventilation target variable are set in step a). Provisions may be made in this manner, in particular, for setting the ventilation process to be optimized even better and for adapting this ventilation process to the patient. A first preferred combination of two ventilation parameters is represented, for example, by a combination of PEEP and inspiratory pressure, especially such that a distance between the inspiratory pressure and the positive end-expiratory pressure is constant or at least essentially constant. The difference between PEEP and the inspiratory pressure is thus constant in this case, and the tidal volume varies at the same time. As an alternative, the PEEP and the tidal volume may be combined. The inspiratory pressure will then vary in this case. It may be useful in this connection to limit the distance between PEEP and the inspiratory pressure. Preferred possibilities of combination also arise concerning the ventilation target variables, for example, from the arterial oxygen saturation, which can be set by varying the PEEP and/or the $FiO_2$ and the arterial or end-tidal partial pressure of the carbon dioxide, which can be set by varying the ventilation rate at a fixed tidal volume. An additional preferred possibility is represented by a combination of the arterial oxygen saturation and the alveolar minute volume, and the distance between the PEEP and the inspiratory pressure is frequently also minimized in this case. A combination of the end-expiratory pressure and the alveolar minute volume proved to be preferred concerning a combination of a ventilation parameter and a ventilation target variable. It may be useful in this connection as well to limit or minimize the distance between the PEEP and the inspiratory pressure.

Further, provisions may be made in a process according to the present invention for using at least one of the following variation parameters for setting the variation procedure in step b):
  number of the variation sections,
  duration of the variation sections,
  variation start value,
  variation end value and
  change in the variation value.

This list is specifically incomplete, so that additional variation parameters may also be used to set the variation procedure. A number of variation sections specifies, in particular, how many different variation values of the ventilation parameter to be set shall be checked one after another. A greater number makes it thus possible, in particular, to check a broader range of values for the ventilation parameter and/or to check with a finer gradation between the individual variation values used. A duration of the variation sections specifies, in turn, how long the individual variation sections last. Provisions may be made, in particular, for setting this duration to be long enough, on the one hand, so that transient processes subside at the beginning of the variation section, but to select at the same time the duration to be short enough to be able to avoid an excessively prolonged ventilation of the patient with a suboptimal ventilation parameter. The variation start value and the variation end value specify the limits of the values between which the ventilation parameter shall be varied. The change in the variation value specifies, in turn, how the variation value shall change between the individual variation sections.

A process according to the present invention may preferably be perfected to the effect that a duration of the variation sections is between 10 sec and 60 sec, especially between 20 sec and 45 sec, and it preferably equals 30 sec. These preferred durations of the variation sections, especially a duration of 30 sec, represent especially preferred values. Durations especially between 20 sec and 45 sec and preferably a duration of 30 sec represent especially good compromises between the above-described transient time, during which patient responses to the change in the ventilation parameter subside, and a shortest possible duration of a ventilation of the patient with suboptimal variation values of the ventilation parameter.

Further, a process according to the present invention may be perfected such that a constant change in the variation value is used. In other words, the individual variation sections differ concerning the variation value of the ventilation parameter, which value is used in them, by the same, constant change in the variation value. This can be provided in an especially simple manner in respect to the underlying regulation and/or control of the variation.

As an alternative, provisions may be made for using a variable change in the variation value in a variant of a process according to the present invention, in which case especially variable changes in the variation value with different signs are used. A variable change in the variation value in the sense of the present invention may mean especially that the change in the variation value by which the individual variation values of the ventilation parameter to be set may differ, especially concerning a value of the change in the variation value. For example, the marginal ranges of the checked parameter space of the ventilation parameter to be set are checked, especially close to the start value of the variation or close to the end value of the variation, with greater distances between the variation values used, i.e., with changes in the variation value having higher values, and a middle range of the parameter space is checked by a finer change in the variation value having lower values. This may especially preferably be carried out when a properly set ventilation parameter shall be improved even more and this parameter is located in the middle or at least essentially in the middle of the parameter space being checked. An even more accurate and finer setting of the ventilation parameter to be set can be made possible in this manner. Different signs of the change in the variation value, especially in consecutive variation sections, cause, in particular, the ventilation parameter to be set not to change continuously in one direction during the variation, but the variation values of the ventilation parameter will have jumps, and to both increase and decrease especially in the course of the performance of the variation. For example, habituation effects occurring during the performance of the variation at the variable ventilation parameters can be avoided in this manner in the response of the patient to the changed ventilation.

A process according to the present invention may also be configured such that at least one of the following comparison criteria is used in step e) for determining the quality parameter of the ventilation process in each of the at least two variation sections:
  Euclidean distance of the centers of the ventilation distribution and of the perfusion distribution,
  distance of the centers of the ventilation distribution and of the perfusion distribution in the ventrodorsal direction, similarity indicator of the ventilation distribution and perfusion distribution, comparison metric, and comparison with existing and/or simultaneously determined simulation results.

This list is specifically incomplete as well, so that additional comparison criteria may also be used to determine the quality parameter of the ventilation process. The centers of the ventilation distribution and of the perfusion distribution represent first clues each to the distribution of ventilation and perfusion in the lungs or in the lung tissue of the patient. A Euclidean distance of the centers or a distance of the centers, limited to the ventrodorsal direction, thus make possible a first, simple determination of the quality parameter, a smaller distance representing a closer similarity of the two distributions. In particular, special similarity indicators or comparison metrics, in which the entire distributions are taken into consideration, may be used for an even more accurate determination of the quality parameter. The behavior of the lungs during the ventilation process can be calculated for many different ventilation parameters by existing and/or simultaneously established simulation models. The input parameters of these simulations are the ventilation distribution and the perfusion distribution measured in EIT at the respective ventilation settings, together with the respiratory rate, the tidal volume (alternatively and even better: curves of the airway pressure and of the gas volume flow at the patient's mouth), with the cardiac minute volume (determined from the EIT or by an external monitor) and with the relative percentage of oxygen in the inspiratory gas volume flow ($FiO_2$), as well as with estimations or measurements of the partial pressures or of the oxygen and carbon dioxide concentrations in the mixed venous and/or arterial blood. As a result of these simulations, an indicator is, in particular, also outputted in most cases for the effectiveness of the ventilation, which indicator is preferably the volume of the gases oxygen and/or carbon dioxide exchanged in the entire lung or in a certain area of the lungs. The comparison of these simulation results thus makes it likewise possible to determine especially good variation values of the ventilation parameter and hence of an especially high quality parameter of the ventilation process in question during the variation section. In particular, a visual display of the lung functions can also be made possible by such simulations. In particular, it is thus possible, for example, to visualize the distribution of the exchanged gas volume flows of, for example, oxygen and carbon dioxide, especially for different ventilation parameters. A ventilation process, adapted especially specifically to the particular patient, can be planned in this manner for a patient already prior to a ventilation.

A process according to the present invention may also be perfected such that the ventilation distribution and the perfusion distribution are standardized for the use of a similarity indicator for determining the quality parameter, especially such that the ventilation distribution is standardized with the use of a tidal volume and the respiratory rate and the perfusion distribution is standardized with the use of a cardiac minute volume. A plurality of breathing cycles of the ventilation process are usually carried out during a variation section, and the respiratory rate and the tidal volume are not necessary equal in the individual variation sections. In addition, the changing transpulmonary pressure also leads to changes in the cardiac minute volume between the variation sections. A standardization to values that were actually determined for the individual variation sections thus makes possible an especially meaningful absolute ventilation distribution and absolute perfusion distribution. The variation sections are, in turn, also more comparable with one another due to a standardization of all variation sections. An influence of external effects, which cause changes especially in the respective determined ventilation distributions and perfusion distributions in the individual variation sections, can be reduced or even ruled out hereby. The product of the respiratory rate and the tidal volume, which corresponds to the gas volume arriving in the alveoli per unit of time, and the cardiac minute volume, which corresponds (if ignoring the shunt) to the blood volume perfusing the pulmonary capillaries per unit of time, proved, in particular, to be especially suitable for carrying out such standardizations of ventilation distributions and perfusion distributions.

Moreover, a process according to the present invention may be perfected such that at least one of the following similarity indicators is used:

Minkowski distance, inner product, standardized inner product (cosine), and

Kullback-Leibler divergence.

This list is specifically incomplete, so that additional similarity indicators may be used as well. The individual similarity indicators listed have especially different computing requirements, so that a correspondingly fitting similarity indicator can be used depending on the value and the fineness of the ventilation distributions and perfusion distributions determined in the course of a process according to the present invention and/or adapted to the available computing capacity. For example, a Minkowski distance represents a distance of the two distributions or of parts of the two distributions in an n-dimensional space. Similarly to the Euclidean distances, the similarity of two distributions also increases with the decrease in their Minkowski distance. An inner product or a standardized inner product may be considered to be a scalar product of the individual elements of the distributions. This scalar product and hence the inner product assume, in particular, especially high values as the similarity of the distributions being considered increases. The Kullback-Leibler divergence becomes, by contrast, smaller as the similarity of the distributions being considered increases.

According to another variant of a process according to the present invention, provisions may furthermore be made for dividing the ventilation distribution into at least one first ventilation subdistribution and a second ventilation subdistribution by comparison with at least one ventilation limit value and the perfusion distribution into at least one first perfusion subdistribution and a second perfusion subdistribution by comparison with at least one perfusion limit value for the use of a comparison metric for determining the quality parameter. Such a division of the distributions into subdistributions may be performed especially preferably such that the subdistributions are filled correspondingly when the corresponding value of the distribution is higher or lower than the respective limit value being considered. If only a single ventilation limit value or perfusion limit value is used now, it is possible to speak of a binarization of the two distributions. The two subdistributions are obtained now as more or less contiguous point sets, which are especially well suited for a comparison by a comparison metric.

In particular, a process according to the present invention may be perfected such that at least one of the following comparison metrics is used:

Jaccard index,

Dice coefficient, and

Hausdorff distance.

This list is specifically incomplete so that additional comparison metrics may be used as well. A calculation of these different comparison metrics also imposes different requirements on the computer, by which the comparisons shall be carried out. The correspondingly adapted comparison metric can be selected depending on the value and the fineness of the distributions and/or adapted to the available computing capacity. The Jaccard index and the Dice coefficient are based especially on a comparison of the intersection of the compared distributions with the union thereof, and a division according to N-tuples and the values thereof is carried out especially in case of a Dice coefficient. It applies to both comparison metrics that the similarity of the distributions being considered increases as the result of the comparison approaches 1. A Hausdorff distance describes, in turn, a distance of non-empty subsets of the distributions, and this Hausdorff distance can be used especially preferably in case of, for example, binarized distributions. Just as in all other distances, especially small values mean especially similar distributions in the case of the Hausdorff distance.

Further, provisions may be made in a process according to the present invention for the quality parameters determined in step e) to be compared in step f) with a desired quality parameter, the best quality parameter coming closest to the desired quality parameter. This comparison of the individual determined quality parameters with a desired quality parameter may be carried out especially as an alternative or in addition to the comparison of the determined quality parameters with one another. In particular, the individual quality parameters determined are compared in this embodiment of a process according to the present invention with a fixed desired quality parameter preferably determined in advance. This can often be carried out in a shorter computing time than a comparison of the individual quality parameters with one another. Information can also be provided on how to assess the value of the quality parameters determined at least in essentially absolute terms, especially by their distance to the quality parameter.

Moreover, provisions may be made in a process according to the present invention for the parameter value to be displayed in step g) on an output unit and/or to be transmitted as a control parameter to the ventilator for setting the ventilation process. By being displayed on an output unit, for example, a display screen unit, the result of the carrying out of a process according to the present invention can be made available for reading by a user in an especially simple manner. Information on the determined parameter value of the ventilation parameter to be set can be provided in this manner for a user in an especially simple manner. Due to an alternative or additional transmission of control parameters to a ventilator, direct actuation of the ventilator can be made possible for carrying out and setting the ventilation process with the parameter value of the ventilation parameter to be set, which parameter value was determined by a process according to the present invention. This represents an especially rapid implementation of the ventilation process with the parameter value of the ventilation parameter to be set, which parameter value was determined in the process according to the present invention, and an especially low fault liability can be made possible due to the automated computer-based transfer of the control parameter. The parameter value determined can especially preferably be both outputted visually and transmitted electronically as a control parameter. Moreover, the information determined concerning the parameter value of the ventilation parameter to be set may be stored in an internal or external memory.

The output unit may especially preferably be configured for this purpose as a wired or wireless interface for transmitting electronic data.

Moreover, provisions may be made in a process according to the present invention for the ventilation parameter set in step a) and/or the variation procedure set in step b) and/or the variation carried out in step c) and/or the ventilation distributions and perfusion distributions determined in step d) and/or the quality parameters determined in step e) to be displayed on an output unit. An output unit may be a display screen and/or a wired or wireless interface for transmitting electronic data in this case as well. Storage in an internal and/or external memory of the individual pieces of information is conceivable here as well. Especially comprehensive information on the performance of a process can be provided in this manner, currently for a user and/or for a subsequent reproduction and/or for checking of the process carried out.

Furthermore, provisions may be made in a process according to the present invention for using at least one of the following types of additional patient information in step a) for setting the ventilation parameter and/or in step f) for determining the variation section with the best quality parameter in addition to the EIT data:

age,
sex,
height,
body weight,
BMI,
patient's condition,
disease state,
data of other imaging processes,
mean airway pressure,
relative percentage of oxygen in the inspiratory gas volume flow ($FiO_2$),
(mixed venous and/or arterial) oxygen saturation and oxygen partial pressure, and
(mixed venous and/or arterial and/or end-tidal) concentration and partial pressure of carbon dioxide This list is not complete, so that additional patient information may be used as well. An even better adjustment of the ventilation parameter, for example, already at the time when the ventilation parameter is set or else, as an alternative or in addition, when the variation section with the best quality parameter is determined, can be made possible in this manner. Other imaging processes may be especially radiological or nuclear medical processes, for example, computed tomography (CT) and positron emission tomography (PET). Diseases or disease states, in which a process according to the present invention can be used especially advantageously, comprise especially ARDS (acute respiratory distress syndrome), COPD (chronic obstructive pulmonary disease), pulmonary edema, pneumothorax, lung resection, pulmonary hypertension, asthma, lung carcinoma as well as pulmonary fibrosis. These diseases and the changes caused by them in the lungs can usually be visualized especially well by an EIT imaging.

According to a second aspect of the present invention, the object is accomplished by an adjusting device for adjusting a ventilation parameter for a ventilation process of a patient, having an analysis unit with a memory, a data input unit connected to the analysis unit in a data-communicating manner for receiving data and a data output unit connected to the analysis unit in a data-communicating manner for outputting data. An adjusting device according to the present invention is characterized in that the data input unit has an input interface for receiving at least EIT data of an EIT device, by the data output unit further having an output interface for outputting at least control parameters to a ventilator for carrying out a ventilation process in a varied manner, and by the analysis unit having a control and computing unit, wherein the control and computing unit is configured to set a ventilation parameter of the ventilation process, which parameter is to be adjusted, and/or a ventilation parameter to be adjusted, as well as a ventilation target variable for indicating the ventilation process and/or the ventilation parameter, to set a variation procedure of a variation of the set ventilation parameter, comprising at least two variation sections with a respective different variation value of the ventilation parameter, to provide a control parameter via the output interface of the data output unit for carrying out the set variation of the set ventilation parameter on the basis of the set variation procedure, to determine a ventilation distribution in the lungs and a perfusion distribution in the lungs from the collected EIT data received by the receiving interface of the data input unit for each of the at least two variation sections carried out, to compare respective determined ventilation distributions and perfusion distributions for each of the at least two variation sections carried out for determining a quality parameter of the ventilation process in each of the at least two variation sections, wherein the quality parameter corresponds or at least essentially corresponds to a similarity of the particular ventilation distribution and perfusion distribution, to determine the variation section with the best quality parameter by a comparison of the quality parameters determined for each of the at least two variation sections carried out, and to output the variation value of the determined variation section with the best quality parameter as the parameter value for the set ventilation parameter, which is to be adjusted, through the output interface.

Ventilation of a patient by a ventilator requires setting and continual monitoring. It can be made possible, in particular, by an adjusting device according to the present invention to carry out this ventilation process with a ventilation parameter adapted to the patient as best as possible. For the communication with additional elements of the patient care system, especially with a ventilator and with an EIT device for providing EIT data of a thoracic region of a patient, the adjusting device according to the present invention has corresponding data input units and data output units and the corresponding input and output interfaces. The adjusting device according to the present invention has internally an analysis unit with a memory, in which unit, for example, process steps to be carried are stored in a computer (with one or more processors)—and/or machine-readable computer program product.

A control and computing unit makes it possible, in particular, to carry out the necessary steps in order to determine a best possible suitable parameter value for a ventilation parameter for the ventilation process of the patient. The control and computing unit is configured for this to set a ventilation parameter that is to be adjusted. As an alternative or in addition, a ventilation target variable may also be set for the ventilation parameter for indicating the ventilation process by the control and computing unit.

Moreover, the control and computing unit is configured to set a variation procedure of a variation of precisely this ventilation parameter. In other words, a variation procedure, during which a ventilation process of the patient is varied such that it is carried out with different variation values of the ventilation parameter according to the set variation procedure, can be provided by the control and computing unit.

An output interface of the data output unit makes it possible to output control parameters arriving from the control and computing unit, as a result of which the ventilation process can be carried out in the sense of the set variation or of the set variation procedure. An EIT data set of a thoracic region of the patient can preferably be collected according to the present invention by an additional EIT device during each variation section, which is carried out, as was described above, with a respective different variation value of the ventilation parameter. These EIT data are received for each of the at least two variation sections carried out by a receiving interface of the data input unit and are transmitted to the control and computing unit of the analysis unit.

A respective ventilation distribution in the lungs and a perfusion distribution in the lungs or in the lung tissue is determined there from the received EIT data for each of the variation sections. Information on the presence of air in the lungs and in the blood in the surrounding lung tissue can be provided in this manner.

Moreover, the control and computing unit can compare the determined ventilation distributions and perfusion distributions for each of the at least two variation sections with one another in order to determine a quality parameter. Such a quality parameter contains especially information on how similar the two compared distributions are to one another. In other words, the quality parameter increases with increasing similarity of the two distributions. The background of this is especially that an especially good gas exchange between the air in the lungs and in the blood in the lung tissue can, in turn, be inferred from ventilation distributions and perfusion distributions that are especially similar to one another.

In addition, the variation section that has the best quality parameter can be determined by the control and computing unit, this determination being able to be carried out especially by comparison, especially in pairs, of the quality parameters determined. The best quality parameter is especially the quality parameter that corresponds to the distributions that are most similar to one another.

Finally, the adjusting device according to the present invention, especially the control and computing unit of the adjusting device, is configured to output as the parameter value of the ventilation parameter the variation value that this parameter value had during the variation section with the best quality parameter. An especially good setting of the ventilation process to be carried out on the patient can be carried out in this manner based on the determined parameter value of the ventilation parameter.

In summary, a setting of a ventilation parameter of a ventilation process of a patient can thus be improved by an adjusting device according to the present invention. This can also be carried out, in particular, in an automated or at least partially automated manner by an adjusting device according to the present invention, wherein it is possible, for example, to carry out a setting of the individual variation sections of the variation procedure as well the carrying out of the ventilation process by the adjusting device according to the present invention after manually inputting the ventilation parameter to be set. Provisions may also be made for carrying out a process in a fully automated manner by an adjusting device according to the present invention without the compulsory presence of a professional staff, for example, at regular intervals for the continuous checking of the settings of the ventilation process. In particular, an effect of the change in the used value of the ventilation parameter to be adjusted can be determined and monitored by an adjusting device according to the present invention in real time. This may also be carried out especially directly at the hospital bed by the use of the EIT device, without the patient having to be brought to the corresponding imaging devices, for example, a CT device or a PET device, for medical imaging. This may be advantageous especially in the case of patients who require intensive care.

Provisions may especially preferably be made in an adjusting device according to the present invention for the adjusting device to be configured for carrying out a process according to the first aspect of the present invention. All the advantages that were described in detail with reference to a process according to the present invention according to the first aspect of the present invention can thus also be provided by an adjusting device according to the present invention according to the second aspect of the present invention, which adjusting device is configured for carrying out such a process according to the first aspect of the present invention.

An adjusting device according to the present invention may also be perfected such that the analysis unit has an output unit for outputting electrical and/or electronic and/or visual and/or acoustic output information. Transmission of the results, especially of the determined parameter value of the ventilation parameter to be set, can be made possible in this manner. This output information may be transmitted electrically or electronically, for example, directly to a ventilator and/or to an EIT device, especially also already during the variation or for the performance of the variation of the ventilation parameter to be set. A visual and/or acoustic transmission of the output information makes it possible, in particular, to provide the corresponding information for a user of an adjusting device according to the present invention. Corresponding to these possibilities, the output unit may be configured, for example, as an electronic and/or electrical interface, also in a wired and/or wireless manner, and/or as a display screen unit and/or loudspeaker unit.

Further, provisions may be made in an adjusting device according to the present invention for the analysis unit to have at least one input unit for inputting the ventilation parameter to be varied and/or the ventilation target variable and/or for setting the variation procedure. It is possible in this manner, in particular, to provide a possibility of controlling and/or checking the entire procedure or the operation of the adjusting device for a user. It can be made possible in this manner to increase the flexibility, for example, an adaptation of the steps to be performed, to the individual patient. Such an input unit may be configured, for example, as a rotary control, keyboard, switch or the like. Provisions may also be made for integrating the input unit into an output unit, for as a touch-sensitive display screen.

According to a third aspect of the present invention, the object is accomplished by a medical system, having a ventilator, an EIT device as well as an adjusting device for adjusting a ventilation parameter for a ventilation process of a patient. A medical system according to the present invention is characterized in that the adjusting device is configured according to the second aspect of the present invention. An adjusting device according to the second aspect of the present invention may be configured for carrying out the process according to the first aspect of the present invention. A medical system according to the present invention according to the third aspect of the present invention can thus provide all the advantages that were described in detail with reference to an adjusting device according to the second aspect of the present invention or with reference to a process according to the first aspect of the present invention.

Moreover, provisions may be made in a medical system according to the present invention for the adjusting device to be integrated at least partially into the ventilator and/or the EIT device. An especially compact configuration of a medical system can be provided by such an at least partial integration of the adjusting device either into the ventilator or into the EIT device or into both devices. Provisions may be made, in particular, for the adjusting device to be completely integrated into the ventilator or the EIT device.

Further steps improving the present invention appear from the following description of exemplary embodiments of the present invention, which are shown in the figures. All the features and/or advantages appearing from the claims, from the description and from the drawings, including structural details and arrangements in space, may be essential for the present invention both in themselves and in various combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
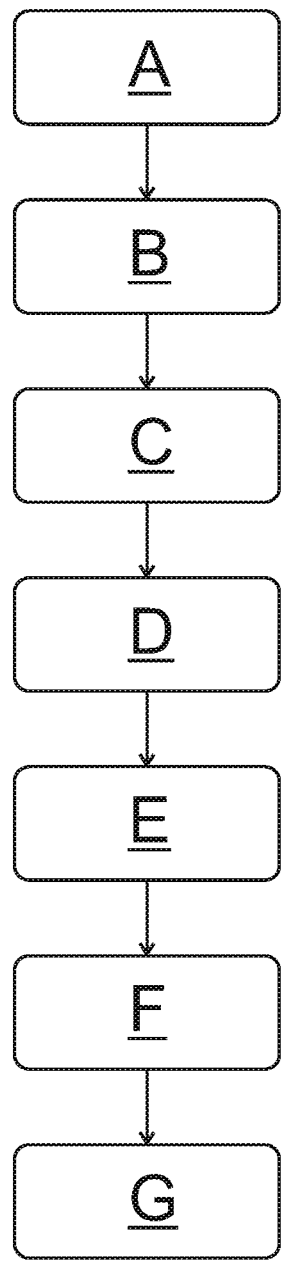
FIG. 1 is a block diagram showing aspects of a process according to the present invention.
Figure 2:
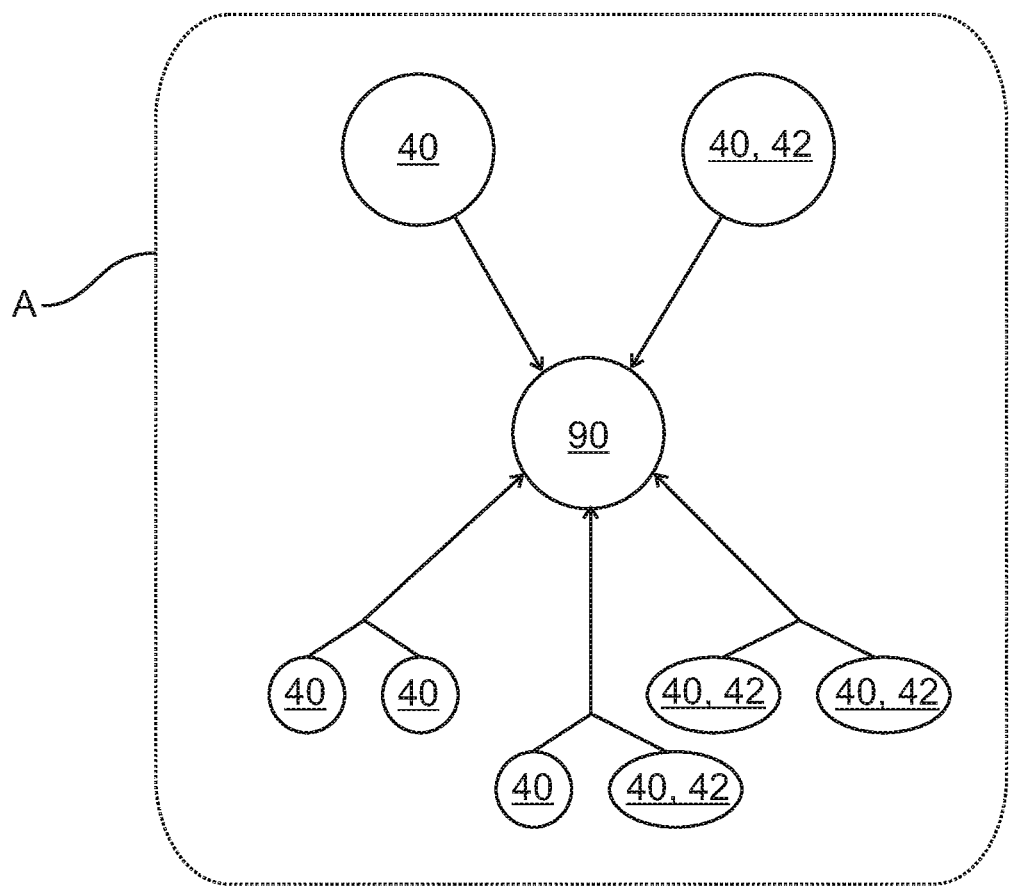
FIG. 2 is a block diagram showing aspects of step a) of a process according to the present invention.

Referring to the drawings, a process according to the present invention is shown in FIGS. 1 through 8, FIG. 1 showing a schematic overview and FIGS. 2 through 8 showing individual steps of the process. The process steps a) through g) are designated by capital letters in FIGS. 1 through 8. FIGS. 1 through 8 will be described below together. The devices necessary for carrying out a process according to the present invention, especially a medical system 100, are shown as an example in FIG. 9.

A ventilation parameter 40 of a ventilation process 90, which parameter is to be adjusted, and/or a ventilation parameter 40, which is to be adjusted, as well as a ventilation target parameter 42 for indicating the ventilation process 90 and/or the ventilation parameter 40, is set in step a) of a process according to the present invention, which step is designated by A in FIG. 1. This may be carried out, for example, by an adjusting device 1 of a medical system 100, as it is shown as an example in FIG. 9. Provisions may be made, in particular, for a combination of at least two ventilation parameters 40 to be set and/or a combination of at least two indicating ventilation target variables 42 and/or a combination of at least one ventilation parameter 40 and at least one indicating ventilation target variable 42 to be also set in this step a). For example, a positive end-expiratory pressure 43 (not shown), an inspiratory pressure, a tidal volume, a ventilation rate, an inhalation time/exhalation time ratio, $FiO_2$ and/or a minute volume may be set as a ventilation parameter 40. An alveolar minute volume, a mean intrathoracic pressure, an (arterial) oxygen saturation or an (arterial) oxygen partial pressure, an (arterial) carbon dioxide saturation or an (arterial) partial pressure of carbon dioxide proved to be suitable as indicating ventilation target variables 42. A setting, which shows which ventilation parameter 40 shall be optimized in the course of the process according to the present invention is thus obtained, in particular, after the end of step a) of a process according to the present invention.

Figure 3:
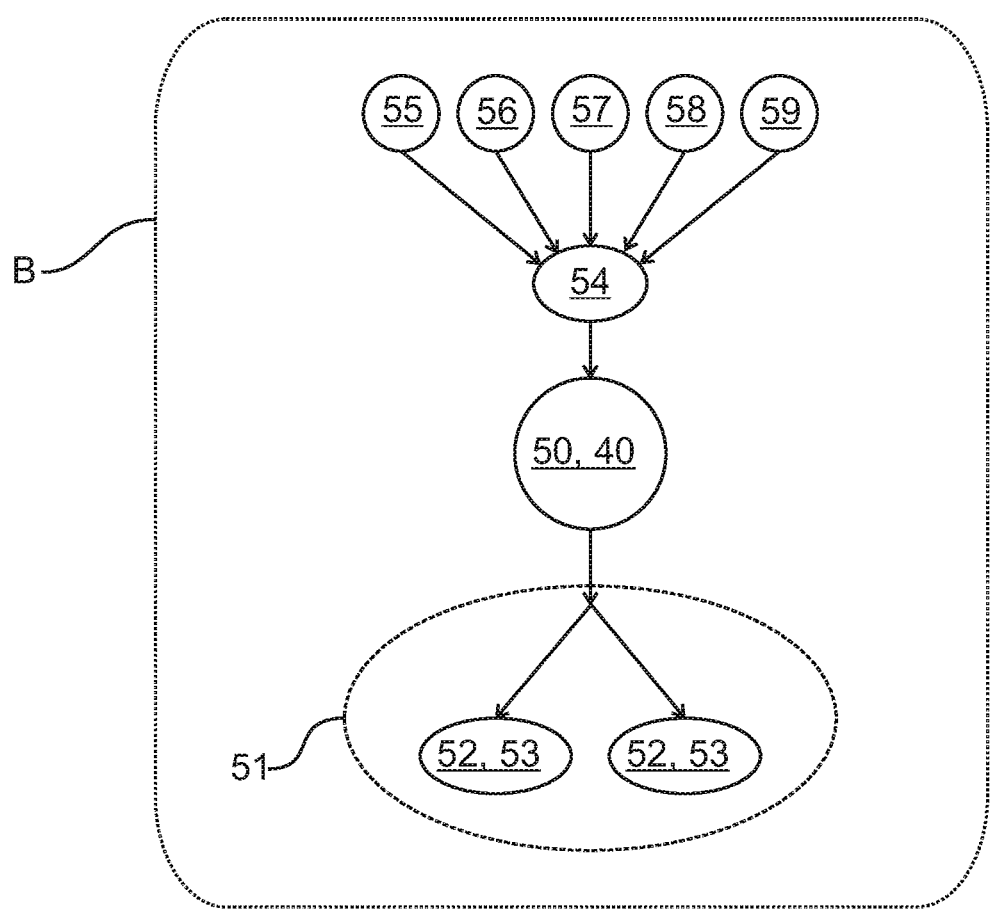
FIG. 3 is a block diagram showing aspects of step b) of a process according to the present invention.

A variation procedure 51 of the variation 50 of the set ventilation parameter 40 is set in the next step b), designated by B in FIG. 1 and explained in more detail in FIG. 3. In particular, many different variation parameters 54, for example, a number 55 of the intended variation sections 52, a duration 56 of the intended variation sections 52, a variation start value 57, a variation end value 58 as well as a change in the variation value 59, can be taken into consideration here. In particular, at least two variation sections 52, in which a respective different variation value 53 each is set for the ventilation parameter 40 to be set, are set for carrying out the variation 50, in other words, for the variation procedure 51. The entire variation 50 and its variation procedure 51 can, in turn, be individually adapted to the patient 110 (not shown) by the corresponding setting and adjustment of the variation parameters 51. For example, a duration 56 of the variation sections 52 can thus preferably be set between 10 sec and 60 sec, especially between 20 sec and 45 sec, and preferably at 30 sec. A change in the variation value 59 may also be set, for example, as a constant or variable value, especially even with different signs. An especially broad range and variability can be provided in this manner when carrying out the variation 50 of the ventilation parameter 40 in the course of a process according to the present invention.

Figure 4:
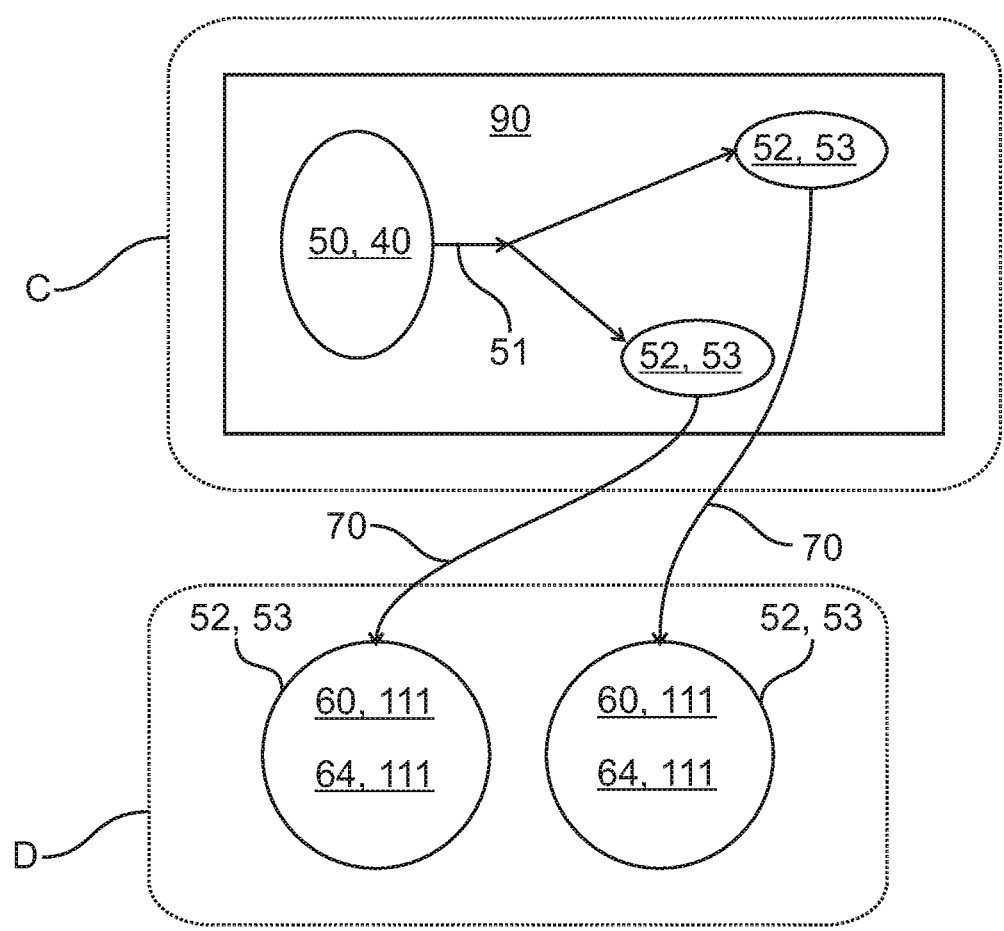
FIG. 4 is a block diagram showing aspects of steps c) and d) of a process according to the present invention.

FIG. 4 shows now steps c) and d) of a process according to the present invention, which are designated by C and D in FIG. 1 and FIG. 4. The variation 50 of the ventilation parameter 40 is carried out in step c) of a process according to the present invention. In other words, the ventilation process 90 is carried out continuously or at least essentially continuously, and by carrying out the variation 50 for the respective individual variation section 52, a ventilation parameter 40 is used, which has a different variation value 53 in each variation section 52. The individual variation sections 52 are carried out especially one after another during the variation procedure 51 of the variation 50. Respective EIT data 70 are determined as a data set by the EIT device 30 for each of the variation sections 52, wherein especially a thoracic region and hence the lungs 111 of the patient 110 (neither of which is shown) are examined and imaged by the EIT device 30. These EIT data 70 are analyzed in the next step d) for each of the variation sections 52 and a ventilation distribution 60 of the lungs 111 as well as a perfusion distribution 64 of the lungs 111 or of the lung tissue of the patient 110 are determined from them. In other words, information showing which ventilation distribution 60 and perfusion distribution 64 are associated with the individual variation values 53 of the ventilation parameter 40 is available after step d) of a process has been carried out.

Figure 5:
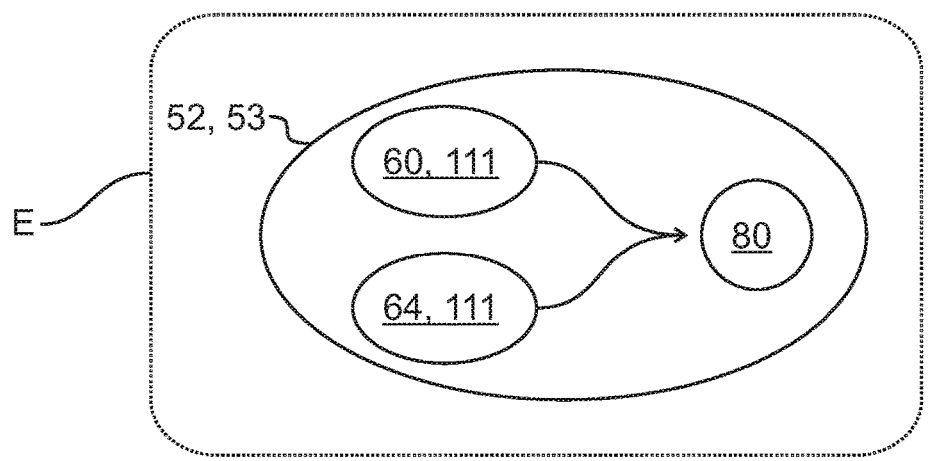
FIG. 5 is a block diagram showing aspects of step e) of a process according to the present invention.
Figure 6:
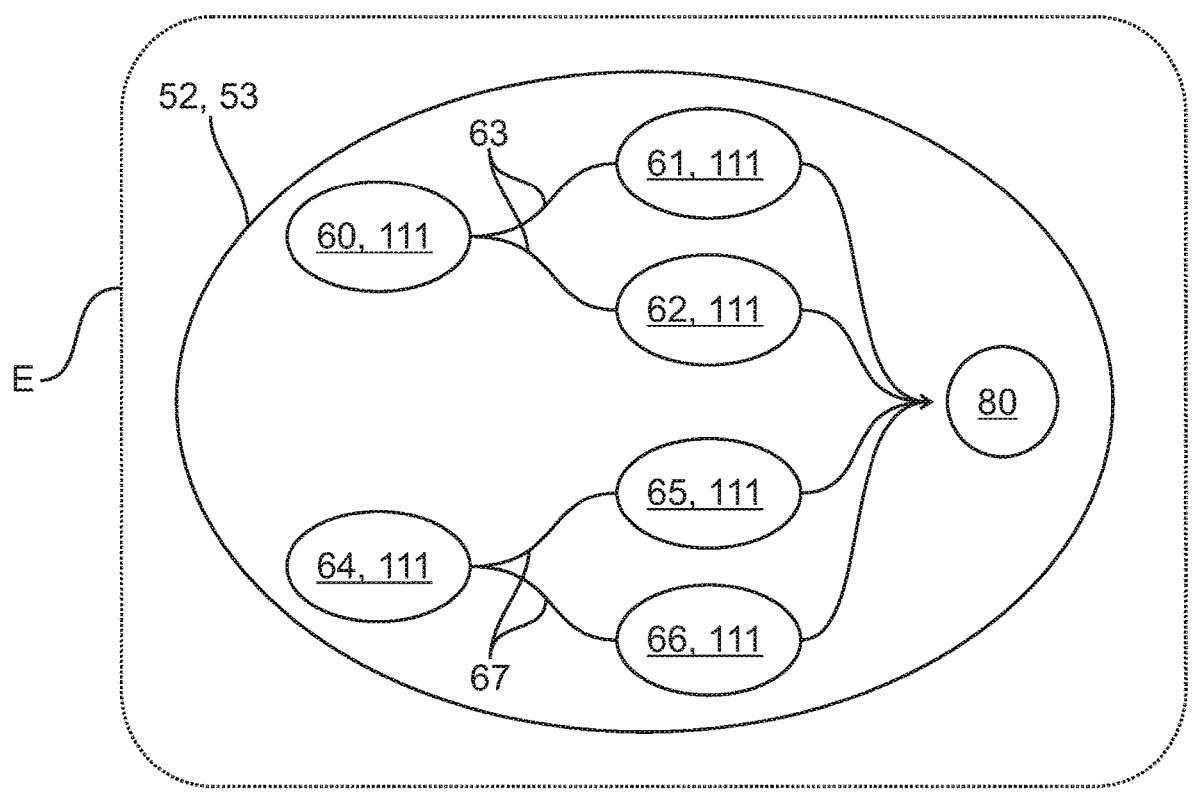
FIG. 6 is a block diagram showing aspects of an alternative embodiment of step e) of a process according to the present invention.

FIG. 5 shows a first possible embodiment of a step e) of a process according to the present invention, designated by E in FIG. 1 and FIG. 5. An individual variation section 52 and its corresponding variation value 53 are shown, the next steps being carried out for each of the variation value steps or variation sections 52. The ventilation distribution 60 as well as the perfusion distribution 64 are thus compared in order to determine a quality parameter 80. This quality parameter 80 corresponds especially at least essentially to a similarity of the two distributions 60, 64. In particular, different comparison criteria, for example, a Euclidean distance of the centers of the ventilation distributions 60 and perfusion distributions 64, a distance of the centers of the ventilation distribution 60 and perfusion distribution 64 in the ventrodorsal direction, or a comparison with existing and/or simultaneously generated simulation data of the individual distributions 60, 64, may be used to determine the quality parameter 80. Further possibilities of a comparison of the distributions 60, 64 are, for example, the use of a similarity indicator of the ventilation distribution 60 and perfusion distribution 64, for example, a Minkowski distance, an inner product, a standardized inner product or a Kullback-Leibler divergence. The ventilation distributions 60 and perfusion distributions 64 may advantageously be standardized in advance, for example, to an alveolar minute volume or to a cardiac minute volume, for a use of such a similarity indicator for determining the quality parameter 80.

Another possibility for determining the quality parameter 80 is represented by comparison metrics, for example, a Jaccard index, a Dice coefficient or a Hausdorff distance. This is shown especially in FIG. 6, in which an alternative embodiment of step e) of a process according to the present invention is shown. Especially the ventilation distributions 60 are divided into a first ventilation subdistribution 61 and a second ventilation subdistribution 62 by comparison with a ventilation limit value 63 for a use of such a comparison metric in this embodiment of step e) of a process according to the present invention. The perfusion distribution 64 was correspondingly divided into a first perfusion subdistribution 65 and a second perfusion subdistribution 66 by comparison with a perfusion limit value 67. An especially suitable use can be made possible for a comparison metric for determining a quality parameter 80 by a comparison, especially in pairs, of the ventilation subdistributions 61, 62 with the perfusion subdistributions 65, 66. An especially high quality parameter 80 means an especially close agreement or similarity of the respective subdistributions 60, 61, 65, 66 and of the underlying distributions 60, 64 here as well.

Figure 7:
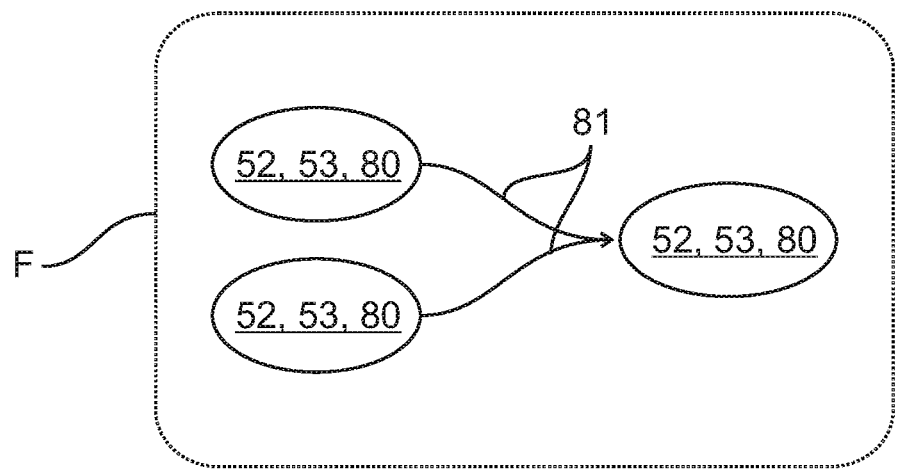
FIG. 7 is a block diagram showing aspects of step f) of a process according to the present invention.

The next step f) of a process according to the present invention is shown in FIG. 7 and is designated specifically by F in FIG. 1 and FIG. 7. Step f) comprises especially a determination of the variation section 52 that has the best quality parameter 80. The individual quality parameters 80 of the individual variation sections 52, shown here as an example for two variation sections 52, are compared for this purpose with a desired quality parameter 81. The variation section 52 whose quality parameter 80 comes closest to the desired quality parameter 81 is considered here to be the variation section 52 with the best quality parameter 80. In other words, information showing the variation section 52 in which the closest similarity prevailed between the ventilation distribution 60 and the perfusion distribution 64 in the lungs 111 of the patient 110 is available after carrying out step f) of a process according to the present invention. Since an especially effective gas exchange between the gas in the alveoli of the lung tissue 111 and in the blood in the blood vessels (capillaries) of the lung tissue, which enclose the alveoli, can be inferred from a close similarity of these distributions 60, 64, this also makes it possible to infer that the ventilation parameter 40 or the variation value 53 thereof is or could be most suitable for the ventilation process 90 of the patient 110.

Figure 8:
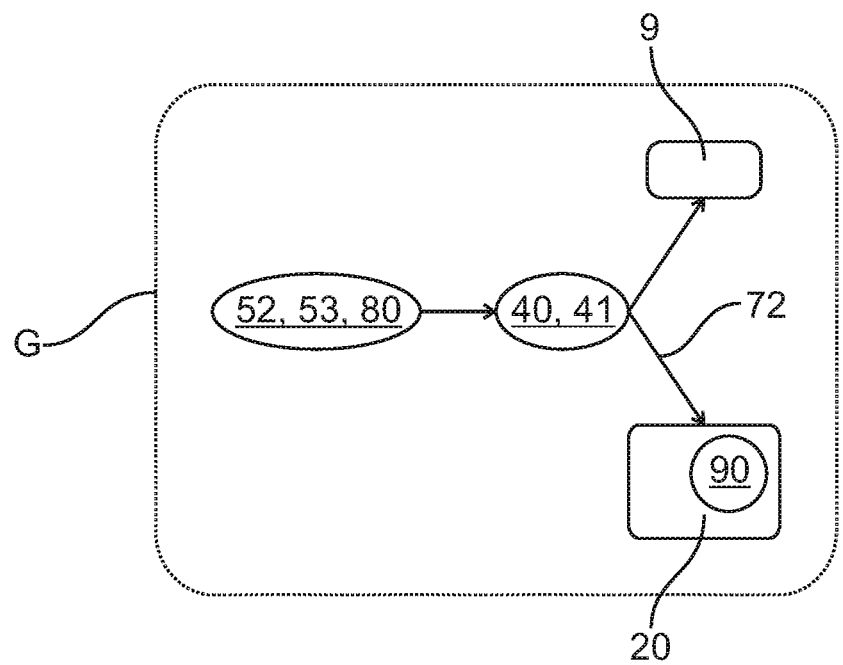
FIG. 8 is a block diagram showing aspects of step g) of a process according to the present invention.

The variation value 53 that was used in the variation section 52 determined in step f) is outputted in the last step g) of a process according to the present invention, designated by G in FIG. 1 and FIG. 8, as the parameter value 41 of the ventilation parameter 40, which value is to be set. This may be outputted to a user, for example, via an output unit 9 as optical and/or acoustic information. As an alternative or in addition, this information may also be transmitted directly as a control parameter 72 to a ventilator 20 via an electrical and/or electronic interface in order to carry out a corresponding ventilation process 90 based on the determined ideal parameter value 41 of the ventilation parameter 40.

In summary, a determination of an ideal parameter value 41, which can at least essentially be automated, can thus be carried out for a special ventilation parameter 40 by a process according to the present invention. As an essential feature of the present invention, the selection of the best parameter value 41 is based on an analysis of EIT data 70 of an EIT device 30, which are collected and analyzed for each variation section 52 of a variation 50 of the ventilation parameter 40 of a thoracic region of a patient 110. Not shown but nevertheless covered by the present invention is the fact that additional information, for example, the ventilation parameter 40 itself and/or the set variation procedure 51 and/or the respective variation 50 carried out and/or the determined ventilation distributions 60 and perfusion distributions 64 and/or the determined quality parameter 80, may also be outputted on an output unit 9 in addition to the determined parameter value 41 of the ventilation parameter 40. Additional patient information 71, for example, age, sex, height, body weight, BMI, patient status, disease state, data of other imaging processes, mean airway pressure, relative percentage of oxygen in the inspiratory gas volume flow ($FiO_2$), (mixed venous and/or arterial) oxygen saturation or (mixed venous and/or arterial) oxygen partial pressure and/or (mixed venous and/or arterial and/or end-tidal) carbon dioxide concentration or (mixed venous and/or arterial and/or partial pressure of the carbon dioxide, may also be used already for setting the ventilation parameter 40 and/or for determining the variation section 52 with the best quality parameter 80 in addition to the EIT data 70. An even better and more individual adjustment of the ventilation parameter 40 to be set can be made possible in this manner.

Figure 9:
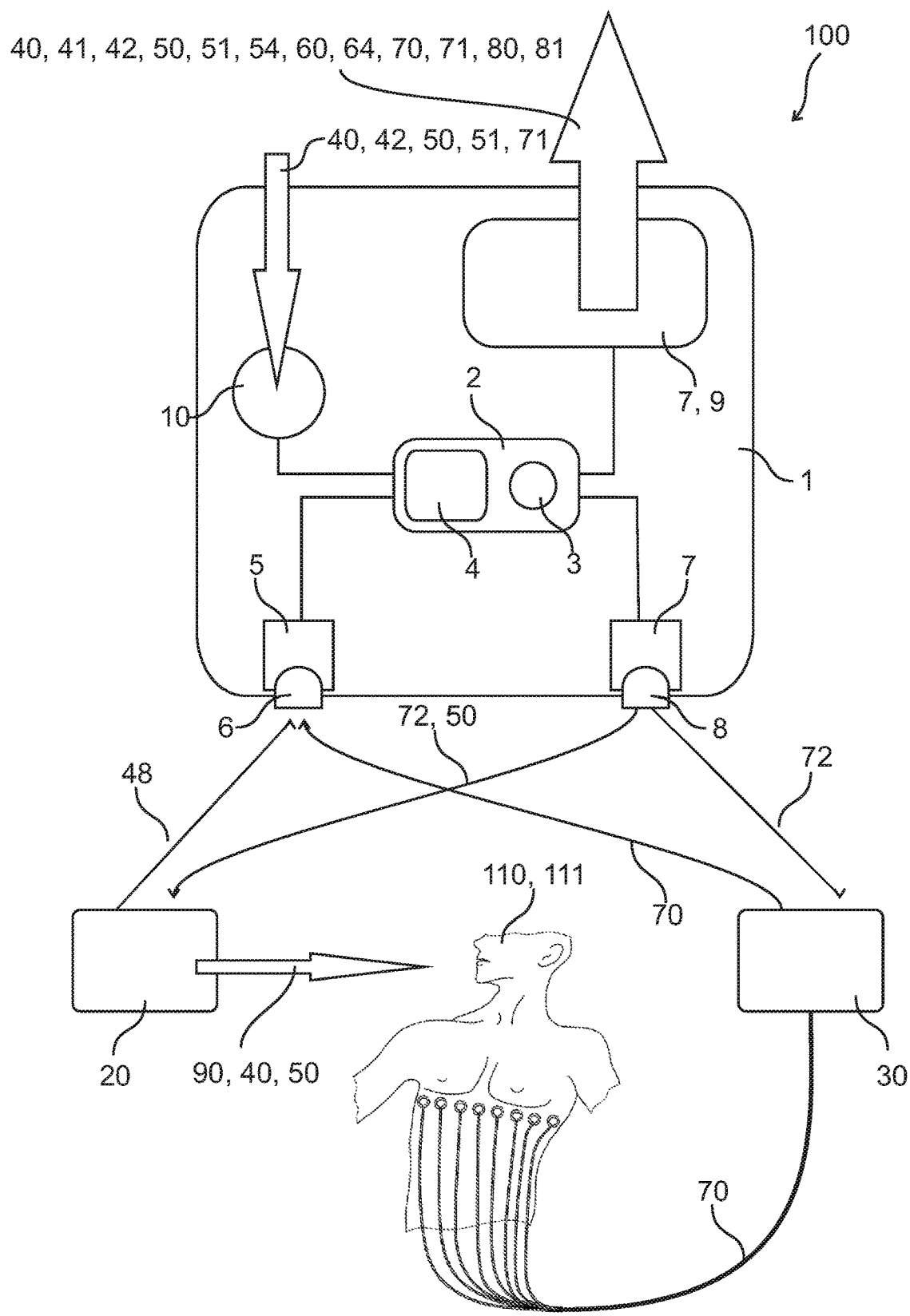
FIG. 9 is a schematic view of a medical system according to the present invention.

FIG. 9 shows a medical system 100 according to the present invention, which has especially an adjusting device 1 according to the present invention. Further, the medical system 100 has a ventilator 20 as well as an EIT device 30. A ventilation process 90 of a patient 110 can be carried out by the ventilator 20. The EIT device 30 is configured, in turn, for determining EIT data 70, especially of a thoracic region of the patient 110, for monitoring a ventilation distribution and a perfusion distribution (neither of which is shown) in the lungs 111 or in a lung tissue of the patient 110. An analysis unit 2 with a memory 3 is a key component of an adjusting device 1 according to the present invention. For example, control commands for executing a process according to the present invention may be stored as machine-readable computer program product in this memory 3, as a result of which an adjusting device 1 according to the present invention is configured for carrying out a process according to the present invention. In other words, all steps of a process according to the present invention can be executed especially by a control and computing unit 4 comprising one or more processors. A ventilation parameter 40 or a ventilation target variable 42 of a ventilation process 90, which process shall be optimized, can thus be set. In order to make this possible and/or even better, an adjusting device 1 according to the present invention may have an input unit 10, via which, for example, the ventilation parameter 40, the ventilation target variable 42, a variation 50 to be carried out and the procedure 51 thereof, as well as additional patient information 71 can be inputted. An especially good and patient-adapted variation procedure 51 of the variation 50 can be set in this manner. The variation 50 of the ventilation parameter 40 is subsequently performed by the adjusting device 1 of the medical system 100 according to the present invention while the ventilation process 90 is being carried out. In other words, the ventilation process 90 of the patient 110 is carried out, and the variation values 53 (not shown) of the ventilation parameter 40 are varied correspondingly depending on the set variation procedure 51. This may be made possible, for example, via a data output unit 7, especially an output interface 8 of the data output unit 7, via which control parameters 72, especially ones comprising the variation 50, can be transmitted to the ventilator 20. At the same time, these control parameters 72 may also be transmitted to the EIT device 30 in order to ensure a corresponding recording of EIT data 70 during the individual variation sections 52. At least EIT data 70 are sent for each of the variation sections 52 to a data input unit 5 of the adjusting device 1 according to the present invention, especially one having an input interface 6. In addition, ventilation data 48 can also be provided by the ventilator 20 for the adjusting device 1. On the one hand, the EIT data 70 can then be analyzed by the control and/or computing unit 4 of the analysis unit 2 such that a ventilation distribution 60 as well as a perfusion distribution 64 can be determined for each of the variation sections 52. These distributions 60, 64 are then preferably compared with one another by the control and/or computing unit 4 of the analysis unit 2, and a quality parameter 80 is determined corresponding to their similarity. The individual quality parameters 80 of the different variation sections 52 are compared in order to determine the variation section 52 with the best quality parameter 80. As an alternative or in addition, a comparison of the individual quality parameters 80 with a desired quality parameter 81 may be provided as well, in which case the variation section 52 whose quality parameter 80 comes closest to the desired quality parameter 81 is identified as the variation section with the best quality parameter 80. The corresponding variation value 53, which was used in the variation section 52 having the best quality parameter 80, can be outputted as the result of the variation 50 as a parameter value 41 of the ventilation parameter 40. The data output unit 7 may have, for example, an output unit 9, especially a display screen unit, for this purpose. Additional information, for example, the ventilation target variable 42, the variation 50, the variation procedure 51, the variation parameter 54, the ventilation distribution 60, the perfusion distribution 64, the EIT data 70, the patient information 71, the respective quality parameter 80, and, if used, the desired quality parameter 81, may also be outputted via this output unit 9, especially in addition to the ventilation parameter 40 and the determined parameter value 41 thereof.

In summary, a parameter value 41 of a ventilation parameter 40, which value is as ideal as possible or is at least optimized, can thus be determined for a ventilation process 90 of a patient 110 by a medical system 100 according to the present invention and an adjusting device 1 according to the present invention. This determination may be carried out especially in an at least partially automated manner and by the use of the EIT device 30 also without additional, expensive medical imaging devices, for example, CT devices and/or PET devices directly at the hospital bed.

Figure 10:
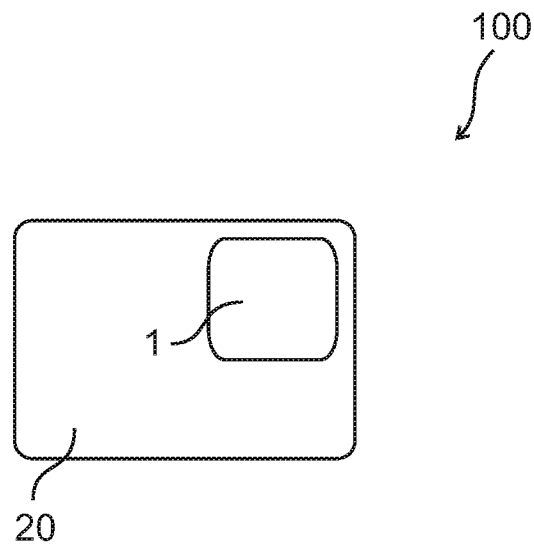
FIG. 10 is a schematic view of a possible embodiment of a ventilator.
Figure 11:
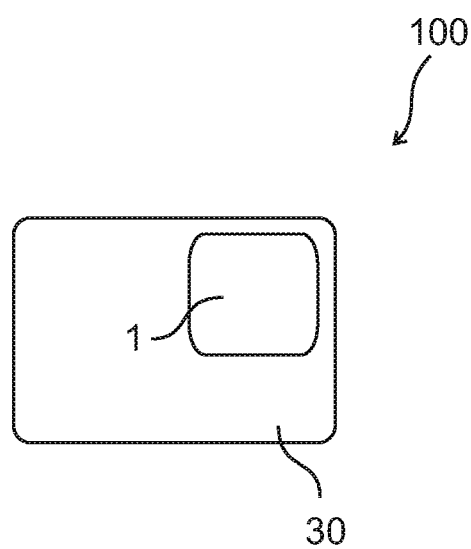
FIG. 11 is a schematic view of a possible embodiment of an EIT device.

Especially preferred embodiments of an adjusting device 1 according to the present invention are shown in FIGS. 10 and 11. The adjusting device 1 according to the present invention, as is shown in FIG. 10, may be integrated, in particular, at least partially into the ventilator 20. An at least partial integration of the device 1 according to the present invention into the EIT device 30, as is shown in FIG. 11, is possible as well. An especially compact configuration of a medical system 100 according to the present invention can be made possible in this manner.

Figure 12:
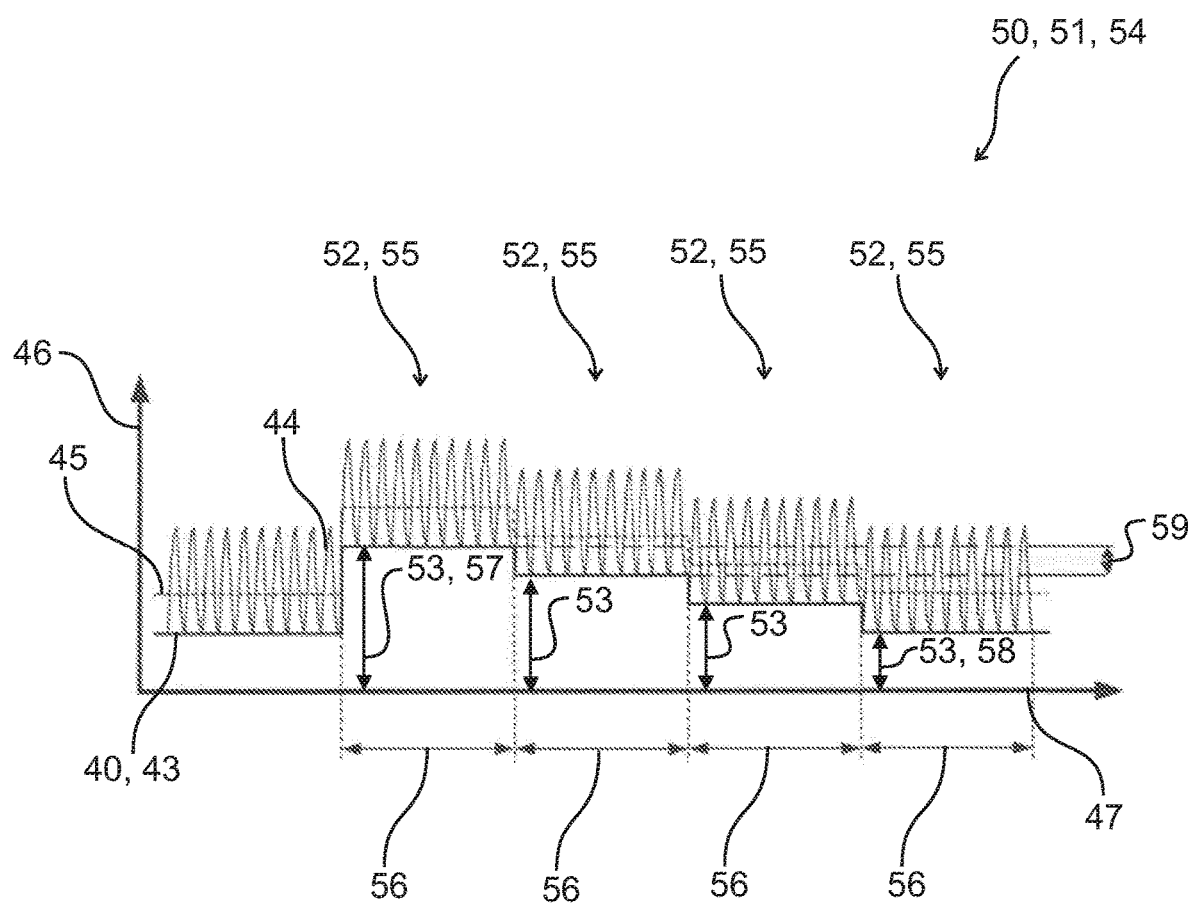
FIG. 12 is a view showing a variation of a ventilator parameter.

FIG. 12 shows a possible performance of a variation 50 of a ventilation parameter 40. The ventilation parameter 40 to be varied is, in particular, a positive end-expiratory pressure 43 in this case. Shown is a diagram in which a pressure 46 is plotted over a time 47, the measured data shown being especially an airway pressure 44 or the mean airway pressure 45. Further, four variation sections 52 of the variation 50 of the ventilation parameter 40, which are carried out during the variation procedure 51 with respective different variation parameters 54 of the ventilation parameter 40, are shown. The number 55 of variation sections 52 is thus selected to be four. As is shown, a continuous change in the variation value 59 may be carried out, as a result of which the variation value 53 decreases continuously and uniformly stepwise from a variation start value 57 to a variation end value 58 in the course of the variation sections 52. The duration 56 of the variation is also selected to be constant, for example, preferably at 30 sec.

Figure 13:
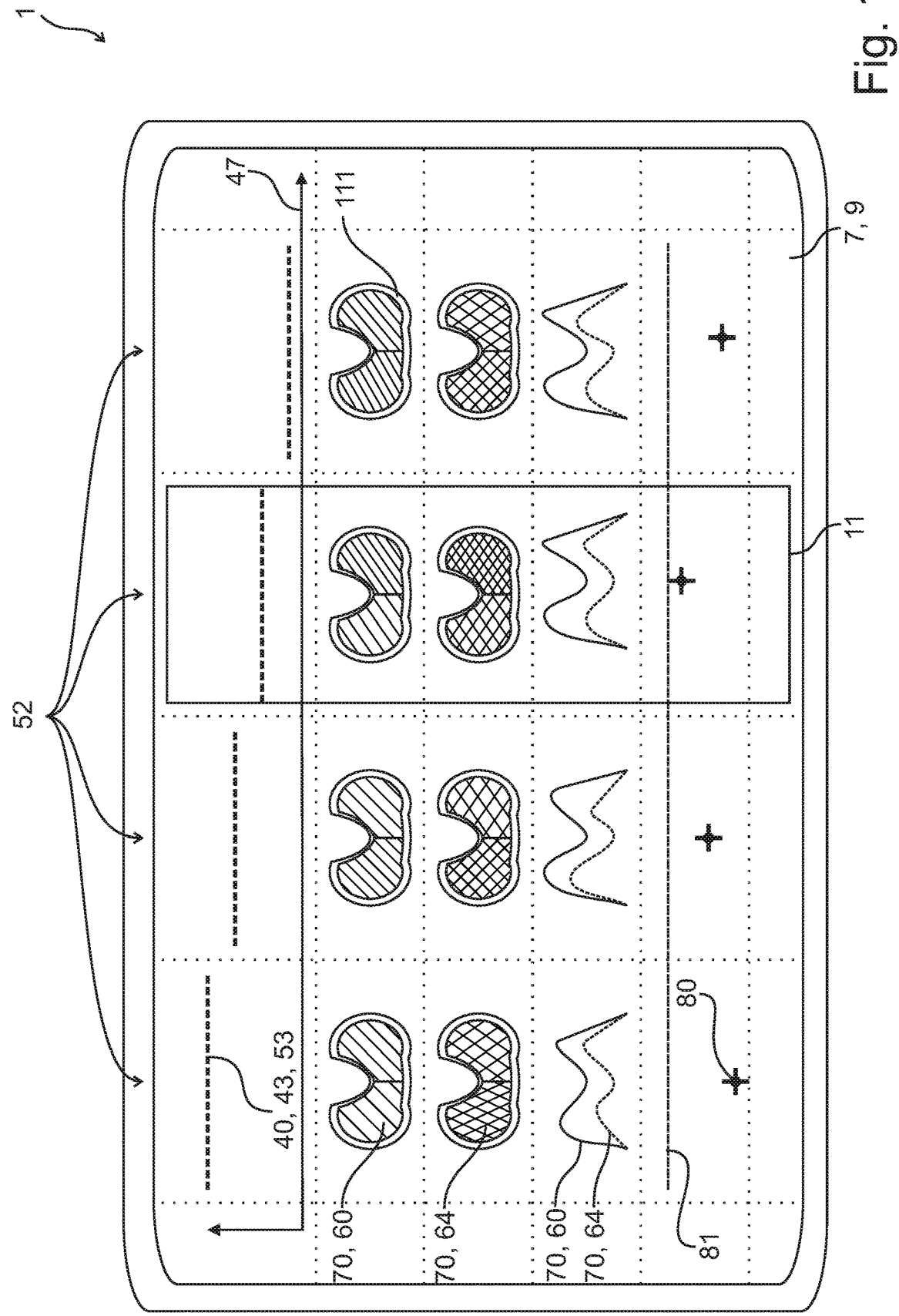
FIG. 13 is a view showing an output unit of an adjusting device according to the present invention during the performance of a process according to the present invention.

FIG. 13 shows a possible display on a data output unit 7 configured as an output unit 9, as it may appear during the performance of the variation 50 shown in FIG. 12. The individual variation sections 52 are shown in columns, but essentially only the elements of the first column are provided with reference numbers for the sake of greater clarity. Thus, the variation value 53 of the ventilation parameter 40 to be set, here of the positive end-expiratory pressure 43, is shown for the individual variation sections 52, especially in the topmost row. The recorded EIT data 70 are shown as ventilation distribution 60 and perfusion distribution 64 in the next three rows, the second row from the top showing a two-dimensional view of the ventilation distributions 60, the third row from the top showing a two-dimensional view of the perfusion distributions 64, and the fourth row form the top showing a one-dimensional projection of both distributions 60, 64. The different distributions 60, 64, which are obtained, as is shown here for both halves of the lungs, left lung and right lung, for the individual variation values 53 of the ventilation parameter 40, are indicated by different shadings in the two-dimensional views. The last row from the top shows the result of an analysis of the distributions 60, 64, especially a determination of a similarity of the two distributions 60, 64. What is shown is especially the respective quality parameter 80 determined and, further, the desired quality parameter 81 used in this embodiment of a process according to the present invention. It is clearly seen that the quality parameter 80 that comes closest to the desired quality parameter 81 is obtained with the use of the variation value 53 in the third variation section 52 from the left. This is also illustrated more specifically by a display frame 11, by means of which a user of the adjusting device 1 according to the present invention, which has the output unit 9 shown, can determine the variation section 52 with the best variation value 53 of the ventilation parameter 40 especially simply, reliably and rapidly.

While specific embodiments of the invention have been shown and described in detail to illustrate the application of the principles of the invention, it will be understood that the invention may be embodied otherwise without departing from such principles.

APPENDIX

List of reference numbers:

| | |
|---|---|
| 1 | Adjusting device |
| 2 | Analysis unit |
| 3 | Memory |
| 4 | Control and computing unit |
| 5 | Data input unit |
| 6 | Input interface |
| 7 | Data output unit |
| 8 | Output interface |
| 9 | Output unit |
| 10 | Input unit |
| 11 | Display frame |
| 20 | ventilator |
| 30 | EIT device |
| 40 | Ventilation parameter |
| 41 | Parameter value |
| 42 | Ventilation target variable |
| 43 | Positive end-expiratory pressure |
| 44 | Airway pressure |
| 45 | Mean airway pressure |
| 46 | Pressure |
| 47 | Time |
| 48 | Ventilation data |
| 50 | Variation |
| 51 | Variation procedure |
| 52 | Variation section |
| 53 | Variation value |
| 54 | Variation parameter |
| 55 | Number |
| 56 | Duration |
| 57 | Variation start value |
| 58 | Variation end value |
| 59 | Change in the variation value |
| 60 | Ventilation distribution |
| 61 | First ventilation subdistribution |
| 62 | Second ventilation subdistribution |
| 63 | Ventilation limit value |
| 64 | Perfusion distribution |
| 65 | First perfusion subdistribution |
| 66 | Second perfusion subdistribution |
| 67 | Perfusion limit value |
| 70 | EIT data |
| 71 | Patient information |
| 72 | Control parameter |
| 80 | Quality parameter |

APPENDIX-continued

List of reference numbers:

| | |
|---|---|
| 81 | Desired quality parameter |
| 90 | Ventilation process |
| 100 | Medical system |
| 110 | Patient |
| 111 | Lungs |

What is claimed is:

1. A process for adjusting a ventilation parameter for a ventilation process of a patient, wherein the ventilation process is carried out by a ventilator, and electrical impedance tomographic (EIT) data of the lungs of the patient, which concern the ventilation process, may be collected by an EIT device, the process comprising the steps of:
setting a ventilation parameter of the ventilation process, which parameter is to be adjusted, or setting a ventilation target variable for indicating the ventilation process and/or indicating the ventilation parameter or setting a ventilation parameter to be adjusted as well as setting a ventilation target variable;
setting a variation procedure of a variation of the ventilation parameter set, the setting of the variation procedure comprising forming at least two variation sections of the ventilation process with a respective different variation value of the ventilation parameter;
carrying out the variation of the ventilation parameter set on the basis of the variation procedure, wherein EIT data of the patient are collected by the EIT device for each of the at least two variation sections;
determining a ventilation distribution in the lungs and of a perfusion distribution in the lungs from the EIT data collected for each of the at least two variation sections;
comparing the ventilation distributions and the perfusion distributions determined for each of the at least two variation sections for determining a quality parameter of the ventilation process in each of the at least two variation sections, wherein the quality parameter corresponds or at least essentially corresponds to a similarity of the respective ventilation distribution and perfusion distribution;
determining the variation section with a best quality parameter by comparison of the quality parameters determined for each of the at least two variation sections; and
outputting a variation value of the variation section determined with the best quality parameter as a parameter value for the ventilation parameter to be set.

2. A process in accordance with claim 1, wherein the ventilation parameter set is at least one of the following ventilation parameters:
positive end-expiratory pressure;
inspiratory pressure;
tidal volume;
ventilation rate;
inhalation/exhalation ratio;
$FiO_2$; and
minute volume.

3. A process in accordance with claim 1, wherein the ventilation target variable set is at least one of the following indicating ventilation target variables:
alveolar minute volume;
arterial oxygen saturation;
arterial oxygen partial pressure;
arterial and end-tidal concentration; and
partial pressure of carbon dioxide.

4. A process in accordance with claim 1, wherein the step of setting a ventilation parameter of the ventilation process, which parameter is to be adjusted, or setting a ventilation parameter to be adjusted as well as setting a ventilation target variable for indicating the ventilation process and/or indicating the ventilation parameter comprises setting:
a combination of at least two ventilation parameters; or
setting a combination of at least two indicating ventilation target variables; or
setting a combination of at least one ventilation parameter and at least one indicating ventilation target variable.

5. A process in accordance with claim 1, wherein the step of setting the variation procedure is based on at least one of the following variation parameters:
a number of the variation sections;
a duration of the variation sections;
a variation start value;
a variation end value; and
a change in the variation value.

6. A process in accordance with claim 5, wherein the step of setting the variation procedure is based on a duration of the variation sections between 10 sec and 60 sec.

7. A process in accordance with claim 5, wherein the step of setting a variation procedure is based on a constant change in the variation value.

8. A process in accordance with claim 5, wherein the step of setting the variation procedure is based on a variable change in the variation value.

9. A process in accordance with claim 1, wherein the step of determining the quality parameter of the ventilation process by comparing the ventilation distributions and the perfusion distributions in each of the at least two variation sections is based on at least one of the following comparison criteria:
Euclidean distance of centers of the ventilation distribution and perfusion distribution;
a distance of centers of the ventilation distribution and perfusion distribution in the ventrodorsal direction;
a similarity indicator of the ventilation distribution and perfusion distribution;
a comparison metric, and
a comparison with existing and/or simultaneously obtained simulation results.

10. A process in accordance with claim 9, wherein the ventilation distribution and the perfusion distribution are standardized for the use of the similarity indicator to determine the quality parameter, wherein the ventilation distribution is standardized based on a tidal volume and a respiration rate and the perfusion distribution is standardized based on a cardiac minute volume.

11. A process in accordance with claim 9, wherein the similarity indicator is at least one of the following similarity indicators:
a Minkowski distance;
an inner product;
a standardized inner product (cosine); and
a Kullback-Leibler divergence.

12. A process in accordance with claim 9, wherein the comparison criteria as a comparison metric to determine the quality parameter for the ventilation distribution is based on dividing the ventilation distribution into at least one first ventilation subdistribution and a second ventilation subdistribution by comparison of the ventilation distribution with at least one ventilation limit value and dividing the perfusion distribution into at least one first perfusion subdistribution and a second perfusion subdistribution by comparison of the ventilation distribution with at least one perfusion limit value.

13. A process in accordance with claim 12, wherein comparison of the ventilation distribution with at least one ventilation limit value and comparison of the ventilation distribution with at least one perfusion limit value is based on at least one of the following comparison metrics:
Jaccard index,
Dice coefficient and
Hausdorff distance.

14. A process in accordance with claim 1, wherein comparison of the quality parameters determined for each of the at least two variation sections comprises comparing each of the quality parameters determined with a desired quality parameter, wherein the best quality parameter is closest to the desired quality parameter.

15. A process in accordance with claim 1, wherein the step of outputting comprises:
displaying the parameter value on a display unit; or
transmitting the parameter value as a control parameter to the ventilator for setting the ventilation process, or
displaying the parameter value on a display unit and transmitting the parameter value as a control parameter to the ventilator for setting the ventilation process.

16. A process in accordance with claim 1, further comprising displaying, on a display unit, one or more of:
the ventilation parameter set;
the variation procedure set;
the variation carried out;
the ventilation distributions and perfusion distributions determined; and
the quality parameters determined.

17. A process in accordance with claim 1, wherein at least one of the steps of setting the ventilation parameter and determining the variation section with the best quality parameter is based on, in addition to the EIT data, one or more of the following:
an age of the patient;
a sex of the patient;
a height of the patient;
a body weight of the patient;
a BMI of the patient;
a condition of the patient;
a disease state of the patient;
data of another imaging processes;
a mean airway pressure of the patient;
a relative percentage of oxygen in the inspiratory gas volume flow ($FiO_2$) of the patient;
mixed venous and/or arterial oxygen saturation and oxygen partial pressure of the patient; and
mixed venous and/or arterial and/or end-tidal concentration and partial pressure of carbon dioxide of the patient.

18. An adjusting device for adjusting a ventilation parameter for a ventilation process of a patient, the adjusting device comprising:
an analysis unit with a memory;
a data input unit data-communicatingly connected to the analysis unit for receiving data at the analysis unit, the data input unit comprising an input interface receiving at least EIT data of an EIT device; and
a data output unit data-communicatingly connected to the analysis unit for outputting data from the analysis unit, the data output unit comprising an output interface for outputting at least control parameters to a ventilator for carrying out the ventilation process as a varied ventilation process, wherein the analysis unit comprises a control and computing unit configured:
to set a ventilation parameter of the ventilation process, which parameter is to be adjusted, or set a ventilation target variable for indicating the ventilation process and/or indicating the ventilation parameter or set a ventilation parameter to be adjusted as well as set a ventilation target variable;
to set a variation procedure of a variation of the ventilation parameter to be set, comprising providing at least two variation sections, each with a respective different variation value of the ventilation parameter;
to provide, via the output interface of the data output unit, a control parameter for carrying out the set variation of the set ventilation parameter on the basis of the set variation procedure;
to determine a ventilation distribution in the lungs and a perfusion distribution in the lungs from the EIT data received through the receiving interface of the data input unit for each of the at least two variation sections carried out;
to compare the respective ventilation distributions and perfusion distributions determined for each of the at least two variation sections carried out for determining a quality parameter of the ventilation process in each of the at least two variation sections, wherein the quality parameter corresponds or at least essentially corresponds to a similarity of the respective ventilation distribution and perfusion distribution;
to determine the variation section with the best quality parameter by comparing the quality parameters determined for each of the at least two variation sections carried out; and
to output the variation value of the determined variation section with the best quality parameter as a parameter value for setting the ventilation parameter through the output interface.

19. An adjusting device in accordance with claim 18, wherein the adjusting device is configured to carry out a process comprising the steps of:
setting a ventilation parameter of the ventilation process, which parameter is to be adjusted, or setting a ventilation parameter to be adjusted as well as setting a ventilation target variable for indicating the ventilation process and/or indicating the ventilation parameter;
setting a variation procedure of a variation of the ventilation parameter set, the setting of a variation procedure comprising forming at least two variation sections with a respective different variation value of the ventilation parameter;
carrying out the variation of the ventilation parameter set on the basis of the variation procedure, wherein EIT data of the patient are collected by the EIT device for each of the at least two variation sections;
determining a ventilation distribution in the lungs and of a perfusion distribution in the lungs from the EIT data collected for each of the at least two variation sections;
comparing the ventilation distributions and the perfusion distributions determined for each of the at least two variation sections for determining a quality parameter of the ventilation process in each of the at least two variation sections, wherein the quality parameter corresponds or at least essentially corresponds to a similarity of the respective ventilation distribution and perfusion distribution;

determining the variation section with a best quality parameter by comparison of the quality parameters determined for each of the at least two variation sections; and outputting a variation value of the variation section determined with the best quality parameter as a parameter value for the ventilation parameter to be set.

20. An adjusting device in accordance with claim 18, wherein the data output unit includes an output unit of the analysis unit for outputting electrical and/or electronic and/or visual and/or acoustic output information.

21. An adjusting device in accordance with claim 18, wherein the data input unit includes an input unit of the analysis unit for inputting the ventilation parameter to be varied and/or the ventilation target variable and/or to set the variation procedure.

22. A medical system comprising;

a ventilator;

an EIT device; and an adjusting device for adjusting a ventilation parameter for a ventilation process of a patient, the adjusting device, the adjusting device comprising:

an analysis unit with a memory;

a data input unit data-communicatingly connected to the analysis unit for receiving data at the analysis unit, the data input unit comprising an input interface receiving at least EIT data of an EIT device; and a data output unit data-communicatingly connected to the analysis unit for outputting data from the analysis unit, the data output unit comprising an output interface for outputting at least control parameters to a ventilator for carrying out the ventilation process as a varied ventilation process, wherein the analysis unit comprises a control and computing unit configured:

to set a ventilation parameter of the ventilation process, which parameter is to be adjusted, or set a ventilation parameter to be adjusted as well as set a ventilation target variable for indicating the ventilation process and/or indicating the ventilation parameter;

to set a variation procedure of a variation of the ventilation parameter to be set, comprising providing at least two variation sections, each with a respective different variation value of the ventilation parameter;

to provide, via the output interface of the data output unit, a control parameter for carrying out the set variation of the set ventilation parameter on the basis of the set variation procedure;

to determine a ventilation distribution in the lungs and a perfusion distribution in the lungs from the EIT data received through the receiving interface of the data input unit for each of the at least two variation sections carried out;

to compare the respective ventilation distributions and perfusion distributions determined for each of the at least two variation sections carried out for determining a quality parameter of the ventilation process in each of the at least two variation sections, wherein the quality parameter corresponds or at least essentially corresponds to a similarity of the respective ventilation distribution and perfusion distribution;

to determine the variation section with the best quality parameter by comparing the quality parameters determined for each of the at least two variation sections carried out; and to output the variation value of the determined variation section with the best quality parameter as a parameter value for setting the ventilation parameter through the output interface.

23. A medical system in accordance with claim 22, wherein:

the adjusting device is at least partially integrated into the ventilator;

the adjusting device is at least partially integrated into the EIT device; or the adjusting device is at least partially integrated into the ventilator and the adjusting device is at least partially integrated into the EIT device.

\* \* \* \* \*